US011224678B2

(12) United States Patent
Benevenia et al.

(10) Patent No.: US 11,224,678 B2
(45) Date of Patent: Jan. 18, 2022

(54) ANTIMICROBIAL COMPOSITION FOR INHIBITING MICROBIAL ORGANISMS IN ALLOGRAFT AND THE METHOD THEREOF

(71) Applicant: Rutgers, The State University of New Jersey, New Brunswick, NJ (US)

(72) Inventors: Joseph Benevenia, Montclair, NJ (US); Sheldon S. Lin, Chatham, NJ (US); Michael Vives, Newark, NJ (US)

(73) Assignee: RUTGERS, THE STATE UNIVERSITY OF NEW JERSEY, New Brunswick, NJ (US)

( * ) Notice: Subject to any disclaimer, the term of this patent is extended or adjusted under 35 U.S.C. 154(b) by 329 days.

(21) Appl. No.: 15/425,617

(22) Filed: Feb. 6, 2017

(65) Prior Publication Data

US 2017/0224871 A1 Aug. 10, 2017

Related U.S. Application Data

(60) Provisional application No. 62/293,064, filed on Feb. 9, 2016.

(51) Int. Cl.

| | |
|---|---|
| ***A61L 27/36*** | (2006.01) |
| ***A61L 2/00*** | (2006.01) |
| ***A61L 27/54*** | (2006.01) |
| ***A61L 101/30*** | (2006.01) |

(52) U.S. Cl.

CPC ......... *A61L 27/3695* (2013.01); *A61L 2/0088* (2013.01); *A61L 27/3604* (2013.01); *A61L 27/3608* (2013.01); *A61L 27/3612* (2013.01); *A61L 27/3687* (2013.01); *A61L 27/54* (2013.01); *A61L 2101/30* (2020.08); *A61L 2300/102* (2013.01); *A61L 2300/404* (2013.01); *A61L 2430/40* (2013.01)

(58) Field of Classification Search

None

See application file for complete search history.

(56) References Cited

U.S. PATENT DOCUMENTS

| | | | | |
|---|---|---|---|---|
| 5,454,886 A * | 10/1995 | Burrell | C23C 14/0688 148/565 |
| 6,013,106 A * | 1/2000 | Tweden | A61L 27/54 623/11.11 |
| 6,113,636 A | 9/2000 | Ogle | |
| 9,238,090 B1 * | 1/2016 | Fette | A61L 27/54 |
| 2013/0028981 A1 | 1/2013 | Gratzer | |
| 2013/0280223 A1 | 10/2013 | Owens | |
| 2014/0147487 A1 | 5/2014 | Walls | |
| 2014/0271779 A1 * | 9/2014 | Bagga | A61L 27/46 424/426 |
| 2017/0106119 A1 * | 4/2017 | Skinner | A61L 27/56 |

FOREIGN PATENT DOCUMENTS

| | | |
|---|---|---|
| JP | 2001-523527 A | 11/2001 |
| JP | 2015113299 A | 6/2015 |
| WO | 08032928 A1 | 3/2008 |

OTHER PUBLICATIONS

International Search Report and Written Opinion, PCT/US17/16789, dated Apr. 21, 2017.

Qayyum et al., The Antimicrobial Activity of Different Zinc Salts, Proceedings S.Z.P.G.M.I vol. 12(1-2) 1998, pp. 8-12. p. IO, Table 2.

Faiz et al., 'Efficacy of Zinc as antibacterial Agent Against Enteric Bacterial Pathogens',. J Ayub Med Coll Abbottabad 2011;23(2). p. 20, col. In21 from bottom.

Aho AJ. Clinical use of bone allografts. Ann Med. 1993;25:403-412.

Lord et al., Infection in bone allografts. Incidence, nature, and treatment. J Bone Joint Surg Am. 1988;70:369-376.

Muscolo DL et al. The use of a bone allograft for reconstruction after resection of giant-cell tumor close to the knee. J Bone Joint Surg Am. 1993;75:1656-1662.

Tomford WW et al. Frozen musculoskeletal allografls. A study of the clinical incidence and causes of infection associated with their use. J Bone Joint SurgAm. 1990;72:1137-1143.).

Mankin HJ et al. Infection in massive bone allografts. Clin Orthop Relat Res. 2005;432:210-216.

Delloye, et al: "Bone Allografts: What They Can Offer and What They Cannot", 2007, The Bone & Joint Journal, vol. 89, No. 5, pp. 574-579.

Maral, et al: "Effectiveness of Human Amnion Preserved Long-Term in Glycerol as a Temporary Biological Dressing", Burns, 1999, 25, pp. 625-635.

* cited by examiner

*Primary Examiner* — Allison M Fox

(74) *Attorney, Agent, or Firm* — Fox Rothschild LLP

(57) ABSTRACT

The present invention is a method for producing allograft tissue by applying an antimicrobial solution to allograft tissue. The antimicrobial solution exhibits antimicrobial activity to make allograft resistant to microbial organisms, such as bacterium.

13 Claims, No Drawings

ANTIMICROBIAL COMPOSITION FOR INHIBITING MICROBIAL ORGANISMS IN ALLOGRAFT AND THE METHOD THEREOF

BACKGROUND OF THE INVENTION

Field of the Invention

The present invention relates in general to a method of mechanically processing allograft to provide improved antimicrobial properties and in particular to a method of using a solution of an antimicrobial composition to make allograft resistant to microbial organisms, such as bacterium.

Description of Related Art

Surgeons are frequently faced with reconstruction challenges caused by bone loss. Although autologous bone is the gold standard for bone restoration, donor site morbidity and limited bone volume have led to increased utilization of allograft bone. Approximately 800,000 bone allograft transplantations are performed yearly in the United States, making bone the second most commonly transplanted tissue as described in Boyce et al. Although bone allograft generally restores bone mass, complications such as graft-host nonunion, fracture, and graft infection are not infrequent as described in Aho A J. Clinical use of bone allografts. Ann Med. 1993; 25:403-412.

Allograft-associated infection often requires removal of infected bone and extensive debridement of the affected site with substantial patient morbidity as described by Muscolo D L et al. The use of a bone allograft for reconstruction after resection of giant-cell tumor close to the knee. J Bone Joint Surg Am. 1993; 75:1656-1662. Most of these allograft associated infections can occur early such as within 4 months (Lord et al., Infection in bone allografts. Incidence, nature, and treatment. J Bone Joint Surg Am. 1988; 70:369-376, Tomford W W et al. Frozen musculoskeletal allografts. A study of the clinical incidence and causes of infection associated with their use. J Bone Joint SurgAm. 1990; 72:1137-1143.), and despite extended antibiotic prophylaxis (Mankin H J et al. Infection in massive bone allografts. Clin Orthop Relat Res. 2005; 432:210-216), the reported incidence remains at 4% to 12% (Lord C F et al). Like metallic implants, allografts act as highly porous, non-cellular, and avascular foreign bodies that are prone to bacterial adhesion.

Approaches have been described for depositing antimicrobial elemental metal and/or metal compounds within a medical article. U.S. Pat. No. 6,113,636 describes chemical, photochemical and electrochemical processes for depositing elemental metal on and in a biocompatible material such as tissue. Three approaches are described for associating elemental metal with tissue and other biocompatible materials under relatively mild conditions. A first approach involves the reaction of metal solutions with a chemical reductant, such as unreacted crosslinking agent, which may be present in or added to the tissue the tissue. A second approach involves photo-reduction of metal compounds in the presence of a biocompatible material. Finally, elemental metal can be deposited by electrochemical reduction.

It is desirable to provide a method for processing allograft tissue without chemical processing to make the allograft resistant to microbial organisms. Chemical processing can have the shortcomings of being harmful to the tissue and require cumbersome or expensive manufacturing.

SUMMARY OF THE INVENTION

An aspect of the present invention is to use antimicrobial solutions in the processing of allograft. Antimicrobial solutions comprising metal compound cleansing or washing solutions have been demonstrated to enhance antimicrobial properties to make bone allograft resistant to bacterium infection. Preferred antimicrobial solutions include a zinc solution including $Zn^{2+}$ ions. $Zn^{2-}$ ions in the allograft can exhibit antimicrobial properties. The antimicrobial activity of $Zn^{2+}$ depends on its concentration and contact duration. Application of the antimicrobial solution by soaking or washing can modify the surface of the allograft and/or provide deep tissue cleaning and penetration of the antimicrobial solution into the allograft.

DETAILED DESCRIPTION

In the first aspect the present invention relates to a method of inhibiting the growth of bacterium in allograft tissue comprising mechanically applying an antimicrobial solution to the allograft. The present invention also relates to controlling or combating microbial organisms, comprising mechanically applying an antimicrobial solution to the microbial organism, wherein the antimicrobial solution exhibits antimicrobial activity.

The term “antimicrobial activity” means in the context of the present invention that the antimicrobial of the invention is active in inhibiting, controlling or combating microbial organisms, including fungal organisms, and/or bacterial organisms, such as gram-positive and gram-negative bacteria. The antimicrobial activity can occur after the allograft is implanted into the body.

In a preferred embodiment, the antibacterial activity is the activity for bacterium selected from the group consisting of *Pseudomonas aeruginosa, Staphylococcus aureus, Aspergillus brasiliensis* spores and *Escherichia coli.*

The present invention also relates to an antimicrobial composition comprising, an antimicrobial agent of the invention and pharmaceutically acceptable vehicles, excipients, diluents, and adjuvants.

Zinc compounds suitable for use in the antimicrobial solution of the present invention include inorganic zinc compounds, such as mineral acid zinc salts. Examples of inorganic zinc compounds include, but are not limited to, zinc chloride, zinc sulfate, zinc phosphate, zinc carbonate, and zinc nitrate, zinc chlorate, zinc chromate or combinations thereof.

Zinc compounds which can be used in the antimicrobial solution can also be zinc salts of organic acids. Examples of organic acid zinc salts include, but are not limited to, zinc acetate, zinc formate, zinc propionate, zinc gluconate, bis(maltolato)zinc, zinc acexamate, zinc aspartate, bis(maltolato)zinc(II) [Zn(ma)2], bis(2-hydroxypyridine-N-oxido)zinc(II) [Zn(hpo)2], bis(allixinato)Zn(II) [Zn(alx)2], bis(6-methylpicolinato)Zn(II) [Zn(6mpa)2], bis(aspirinato)zinc(II), bis(pyrrole-2-carboxylato)zinc [Zn(pc)2], bis(alpha-furonic acidato)zinc [Zn(fa)2], bis(thiophene-2-carboxylato)zinc [Zn(tc)2], bis(thiophene-2-acetato)zinc [Zn(ta)2], (N-acetyl-L-cysteinato)Zn(II) [Zn(nac)], zinc(II)/poly(γ-glutamic acid) [Zn(γ-pga)], bis(pyrrolidine-N-dithiocarbamate)zinc(II) [$Zn(pdc)_2$], zinc(II) L-lactate [$Zn(lac)_2$], zinc(II) D-(2)-quinic acid [$Zn(qui)_2$], bis(1,6-dimethyl-3-hydroxy-5-methoxy-2-pentyl-1,4-dihydropyridine-4-thion-ato)zinc(II) [Zn(tanm)2], β-alanyl-L-histidinato zinc(II) (AHZ), or the like, or combinations thereof. In another embodiment, the organic acid of zinc salt is a naturally occurring fatty acid.

In one embodiment, concentrations of zinc chloride of about 1 mM to about 10 mM can be used as the antimicrobial solution. In an alternative embodiment zinc salts can be used in the antimicrobial solution in concentrations of about 30 mM to about 100 mM.

In one embodiment, allograft bone was soaked in the antimicrobial solution. For example, the allograft bone can be soaked in the antimicrobial solutions for from about 2 hours to about 24 hours, preferably from about 2 hours to about 6 hours. In one embodiment, the antimicrobial solution is applied by soaking the allograft tissue in the antimicrobial solution for about 2 hours to about 24 hours, the antimicrobial solution comprises about 0.1% zinc chloride to about 0.5% zinc chloride, preferably about 0.3% zinc chloride to about 0.5% zinc chloride.

Alternatively, allograft bone was rinsed with the antimicrobial solution such as by The Shake Flask Method (ASTM E2149). For example, the allograft bone can be rinsed in the antimicrobial solution for from about 45 minutes to about 120 minutes.

For purposes of the following description, allograft bone is referred to as an exemplary tissue that may be processed according to the present method. However, those skilled in the art will recognize that other tissues, including but not limited to autograft bone, xenograft bone, allograft cartilage, allograft amniotic tissue, other porous tissues, synthetic porous materials, and various soft tissues, may be processed according to the principles defined herein, without departing from the spirit of the invention exemplified herein by reference to allograft bone material. A suitable allograft cartilage is manufactured by Anthrex as BioCartilage®. In one embodiment, the soft tissue is a ligament or a tendon.

In another embodiment of this aspect, the method of the present invention is used in combination with an allograft method, autograft method, xenograft method, alloplastic graft method, or orthopedic biocomposite method.

In another embodiment of this aspect, the patient is a mammalian animal. In another embodiment of this aspect, the patient is a human.

The invention can be further illustrated by the following examples thereof, although it will be understood that these examples are included merely for purposes of illustration and are not intended to limit the scope of the invention unless otherwise specifically indicated. All percentages, ratios, and parts herein, in the Specification, Examples, and Claims, are by weight and are approximations unless otherwise stated.

EXAMPLES

Example 1

Materials and Methods

A suspension of test organism *Staphylococcus aureus* (ATCC 6538) was obtained by adding colonies on tryptic soy agar and 5% Sheep Blood (BAP) with incubation parameters of 35° C.-37° C., aerobic in 0.85% saline to match a 3.0 McFarland standard. The suspension was exposed to a test substance of zinc chloride at specified concentrations of 0.1%, 0.3% and 0.5% from a 1% stock solution at specified exposure times of 10 minutes, 2 hours, 6 hours and 24 hours at a temperature of 37±1° C. (37.2° C.). Latheen broth and 1% sodium bicarbonate (9.9 mL) was used as a neutralizer. After exposure, an aliquot of the suspension was transferred to the neutralizer and was assayed for survivors. Tables 1-3 show results of controls used in this example.

TABLE 1

CONTROL RESULTS

| | Type of Control | Results |
|---|---|---|
| Purity | *Staphylococcus aureus* (ATCC 6538) | Pure |
| | Neutralizer Sterility Control | No Growth |

TABLE 2

TEST POPULATION CONTROL RESULTS

| | | Results | | | |
|---|---|---|---|---|---|
| Test Organism | Timepoint | CFU/mL | $Log_{10}$ | Average $Log_{10}$ | Geometric Mean |
| *Staphylococcus aureus* (ATCC 6538) | $T_0$ | $3.5 \times 10^6$ | 6.54 | 5.67 | $4.68 \times 10^5$ |
| | 24 Hour | $6.2 \times 10^4$ | 4.79 | | |

CFU = Colony Forming Units

TABLE 3

NEUTRALIZATION CONFIRMATION CONTROL RESULTS

| | | Neutralization Confirmation (CFU) | | Pass/Fail |
|---|---|---|---|---|
| Test Substance | Test Organism | Numbers Control | Test Substance Results | ($Log_{10}$ Difference) |
| Zinc chloride Lot# A0340879 | *Staphylococcus aureus* (ATCC 6538) | 34, 19 | 15, 13 | Pass (0.28) |

CFU = Colony Forming Units

Results

Table 4 shows test results to evaluate antimicrobial effectiveness on *Staphylococcus aureus* for the experiments of this example. Table 5 shows calculated data for percent and Log 10 reduction of the test results shown in Table 4.

TABLE 4

TEST RESULTS FOR *Staphylococcus aureus*

| DILUTION | Exposure Time | | | |
|---|---|---|---|---|
| (VOLUME PLATED) | 10 minutes | 2 hours | 6 hours | 24 hours |
| | Number of Survivors | | | |
| Test Substance: 0.1% Zinc Chloride | | | | |
| $10^0$ (1.00 mL) | T, T | 56, 42 | 22, 23 | 4, 3 |
| $10^0$ (0.100 mL) | T, T | 3, 3 | 3, 4 | 0, 0 |
| $10^1$ (0.100 mL) | T, T | 1, 0 | 2, 0 | 0, 0 |
| $10^2$ (0.100 mL) | 66, 69 | 0, 0 | 0, 0 | 0, 0 |
| $10^3$ (0.100 mL) | 9, 19 | 0, 0 | 0, 1 | 0, 0 |
| Test Substance: 0.3% Zinc Chloride | | | | |
| $10^0$ (1.00 mL) | T, T | 0, 2 | 0, 0 | 0, 0 |
| $10^0$ (0.100 mL) | T, T | 0, 0 | 0, 0 | 0, 0 |
| $10^1$ (0.100 mL) | 60, 57 | 0, 0 | 0, 0 | 0, 0 |
| $10^2$ (0.100 mL) | 5, 6 | 0, 0 | 0, 0 | 0, 0 |
| $10^3$ (0.100 mL) | 1, 3 | 0, 0 | 0, 0 | 0, 0 |
| Test Substance: 0.5% Zinc Chloride | | | | |
| $10^0$ (1.00 mL) | T, T | 2, 0 | 0, 0 | 0, 0 |
| $10^0$ (0.100 mL) | T, T | 0, 0 | 0, 0 | 0, 0 |
| $10^1$ (0.100 mL) | 32, 26 | 0, 0 | 0, 0 | 0, 0 |
| $10^2$ (0.100 mL) | 5, 5 | 0, 0 | 0, 0 | 0, 0 |
| $10^3$ (0.100 mL) | 0, 1 | 0, 0 | 0, 0 | 0, 0 |

T = Too Numerous To Count (>300 colonies)

A value of <1 was used in place of zero for calculation purposes.

TABLE 5

| CALCULATED DATA FOR *Staphylococcus aureus* | | | | | | |
|---|---|---|---|---|---|---|
| Test Substance | Exposure Time | CFU/mL in Test Population Control ($Log_{10}$) | CFU/mL of Survivors | $Log_{10}$ Survivors | Percent Reduction | $Log_{10}$ Reduction |
| 0.1% Zinc Chloride | 10 minutes | $4.68 \times 10^5$ | $6.8 \times 10^5$ | 5.83 | None | None |
| | 2 hours | (5.67) | $4.9 \times 10^2$ | 2.69 | >99.8% | 2.98 |
| | 6 hours | | $2.3 \times 10^2$ | 2.36 | >99.9% | 3.31 |
| | 24 hours | | $4 \times 10^1$ | 1.60 | 99.99% | 4.07 |
| 0.3% Zinc Chloride | 10 minutes | | $5.9 \times 10^4$ | 4.77 | 87.4% | 0.90 |
| | 2 hours | | $1 \times 10^1$ | 1.00 | >99.99% | 4.67 |
| | 6 hours | | <5 | <0.70 | >99.99% | >4.97 |
| | 24 hours | | <5 | <0.70 | >99.99% | >4.97 |
| 0.5% Zinc Chloride | 10 minutes | | $2.9 \times 10^4$ | 4.46 | 93.8% | 1.21 |
| | 2 hours | | $1 \times 10^1$ | 1.00 | >99.99% | 4.67 |
| | 6 hours | | <5 | <0.70 | >99.99% | >4.97 |
| | 24 hours | | <5 | <0.70 | >99.99% | >4.97 |

CFU = Colony Forming Units

The geometric mean and average $log_{10}$ values were used for the population control.

Example 2

Materials and Methods

A suspension of test organism *Staphylococcus aureus* (ATCC 6538) was obtained by adding colonies on tryptic soy agar and 5% Sheep Blood (BAP) with incubation parameters of 35° C.-37° C., aerobic in 0.85% saline to match a 3.0 McFarland standard. The suspension was exposed to a test substance of zinc chloride (4.75 mL) with allograft bone 0.25 g at specified concentrations of 0.3% and 0.5% from a 1% stock solution at specified exposure times of 2 hours, 6 hours and 24 hours at a temperature of 37±1° C. Latheen broth and 1% sodium bicarbonate (9.9 mL) was used as a neutralizer. After exposure, an aliquot of the suspension was transferred to the neutralizer and was assayed for survivors. Tables 6-8 show results of controls used in this example.

TABLE 6

| CONTROL RESULTS | | |
|---|---|---|
| | Type of Control | Results |
| Purity | *Staphylococcus aureus* (ATCC 6538) | Pure |
| | Neutralizer Sterility Control | No Growth |

TABLE 7

| TEST POPULATION CONTROL RESULTS | | | | | |
|---|---|---|---|---|---|
| | | Results | | | |
| Test Organism | Timepoint | CFU/mL | $Log_{10}$ | Average $Log_{10}$ | Geometric Mean |
| *Staphylococcus aureus* (ATCC 6538) | $T_0$ | $1.15 \times 10^6$ | 6.06 | 5.83 | $6.76 \times 10^5$ |
| | 24 Hour | $3.9 \times 10^5$ | 5.59 | | |

CFU = Colony Forming Units

TABLE 8

| NEUTRALIZATION CONFIRMATION CONTROL RESULTS | | | | |
|---|---|---|---|---|
| | | Neutralization Confirmation (CFU) | | Pass/ Fail |
| Test Substance | Test Organism | Numbers Control | Test Substance Results | ($Log_{10}$ Difference) |
| Zinc chloride | *Staphylococcus aureus* (ATCC 6538) | 33, 34 | 30, 21 | Pass (0.12) |

CFU = Colony Forming Units

Results

Table 9 shows test results for *Staphylococcus aureus* for the experiments of this example. Table 10 shows calculated data of percent and Log 10 reduction for the test results shown in Table 9.

TABLE 9

TEST RESULTS FOR *Staphylococcus aureus*

| DILUTION (VOLUME PLATED) | Number of Survivors Exposure Time: 2 hours | | | 6 hours | | | 24 hours | | |
|---|---|---|---|---|---|---|---|---|---|
| | Rep 1 | Rep 2 | Rep 3 | Rep 1 | Rep 2 | Rep 3 | Rep 1 | Rep 2 | Rep 3 |
| Test Substance: 0.3% Zinc Chloride with allograft bone | | | | | | | | | |
| $10^0$ (1.00 mL) | T, T | T, T | T, T | T, T | T, T | T, T | 12, 2 | 23, 25 | 8, 7 |
| $10^0$ (0.100 mL) | T, T | T, T | T, T | T, T | T, T | T, T | 0, 4 | 1, 8 | 0, 0 |
| $10^1$ (0.100 mL) | T, T | T, T | T, T | 117, 151 | 210, 224 | 254, 206 | 0, 0 | 1, 1 | 0, 0 |
| $10^2$ (0.100 mL) | 69, 63 | 54, 71 | 85, 101 | 14, 3 | 33, 30 | 25, 32 | 0, 0 | 0, 0 | 0, 0 |
| $10^3$ (0.100 mL) | 8, 9 | 7, 9 | 13, 12 | 1, 1 | 3, 3 | 3, 5 | 0, 0 | 0, 0 | 0, 0 |
| Test Substance: 0.5% Zinc Chloride with allograft bone | | | | | | | | | |
| $10^0$ (1.00 mL) | T, T | T, T | T, T | T, T | T, T | T, T | 9, 15 | 5, 5 | 5, 3 |
| $10^0$ (0.100 mL) | T, T | T, T | T, T | T, T | T, T | T, T | 3, 2 | 0, 1 | 1, 0 |
| $10^1$ (0.100 mL) | T, T | T, T | T, T | 78, 73 | 67, 66 | 68, 59 | 0, 0 | 0, 0 | 0, 0 |
| $10^2$ (0.100 mL) | 74, 70 | 130, 117 | 86, 74 | 6, 4 | 4, 8 | 2, 2 | 0, 0 | 0, 0 | 0, 0 |
| $10^3$ (0.100 mL) | 15, 9 | 11, 17 | 13, 9 | 1, 0 | 0, 0 | 1, 0 | 0, 0 | 0, 0 | 0, 0 |

Rep = Replicate

T = Too Numerous To Count (>300 colonies)

TABLE 10

CALCULATED DATA FOR *Staphylococcus aureus*

| Test Substance | Exposure Time | CFU/mL in Test Population Control ($Log_{10}$) | CFU/mL of Survivors | $Log_{10}$ Survivors | Geometric Mean (Average $Log_{10}$) | Percent Reduction ($Log_{10}$ Reduction) |
|---|---|---|---|---|---|---|
| 0.3% Zinc Chloride with allograft bone | 2 hours | $6.76 \times 10^5$ (5.83) | $6.6 \times 10^5$ | 5.82 | $7.24 \times 10^5$ (5.86) | No Reduction |
| | | | $6.3 \times 10^5$ | 5.80 | | |
| | | | $9.3 \times 10^6$ | 5.97 | | |
| | 6 hours | | $1.34 \times 10^5$ | 5.13 | $1.91 \times 10^5$ (5.28) | 71.7% (0.55) |
| | | | $2.17 \times 10^5$ | 5.34 | | |
| | | | $2.30 \times 10^5$ | 5.36 | | |
| | 24 hours | | $1.2 \times 10^2$ | 2.08 | $1.32 \times 10^2$ (2.12) | >99.9% (3.71) |
| | | | $2.4 \times 10^2$ | 2.38 | | |
| | | | $8 \times 10^1$ | 1.90 | | |
| 0.5% Zinc Chloride with allograft bone | 2 hours | | $7.2 \times 10^5$ | 5.86 | $8.91 \times 10^5$ (5.95) | No Reduction |
| | | | $1.24 \times 10^6$ | 6.09 | | |
| | | | $8.0 \times 10^5$ | 5.90 | | |
| | 6 hours | | $7.6 \times 10^5$ | 4.88 | $6.92 \times 10^4$ (4.84) | 89.8% (0.99) |
| | | | $6.7 \times 10^4$ | 4.83 | | |
| | | | $6.4 \times 10^4$ | 4.81 | | |
| | 24 hours | | $1.2 \times 10^2$ | 2.08 | $6.17 \times 10^1$ (1.79) | 99.99% (4.04) |
| | | | $5 \times 10^1$ | 1.70 | | |
| | | | $4 \times 10^1$ | 1.60 | | |

CFU = Colony Forming Units

The geometric mean and average $log_{10}$ values were used for the test replicates and population control.

Example 3

Materials and Methods

A suspension of test organism *Staphylococcus aureus* (ATCC 6538) was obtained by adding colonies on tryptic soy agar and 5% Sheep Blood (BAP) with incubation parameters of 35° C.-37° C., aerobic in 0.85% saline to match a 3.0 McFarland standard. The suspension was exposed to a test BioCartilage® from Anthrex substance of 4.75 mL of zinc chloride at specified concentrations of 0.3% and 0.5% containing 0.25 g BioCartilage® at specified exposure times of 6 hours and 24 hours at a temperature of 37±1° C. Latheen broth and 1% sodium bicarbonate (9.9 mL) was used as a neutralizer. After exposure, an aliquot of the suspension was transferred to the neutralizer and was assayed for survivors. The suspension was also exposed to a test Amnion Matrix from Anthrex substance of 9.5 mL of zinc chloride at specified concentrations of 0.3% and 0.5% containing Amnion Matrix (1 count) at specified exposure times of 6 hours and 24 hours at a temperature of 37+−1 C. Latheen broth and 1% sodium bicarbonate (9.9 mL) was used as a neutralizer. After exposure, an aliquot of the suspension was transferred to the neutralizer and was assayed for survivors. A Tables 11-13 show controls used in this example.

TABLE 11

| CONTROL RESULTS | | |
|---|---|---|
| | Type of Control | Results |
| Purity | *Staphylococcus aureus* (ATCC 6538) | Pure |
| | Neutralizer Sterility Control | No Growth |

TABLE 12

| TEST POPULATION CONTROL RESULTS | | | |
|---|---|---|---|
| | | Results | |
| Test Organism | Time Point | CFU/mL | $Log_{10}$ |
| *Staphylococcus aureus* (ATCC 6538) | Time Zero | $1.54 \times 10^6$ | 6.19 |
| | 24 Hours | $9.8 \times 10^4$ | 4.99 |
| | Average $Log_{10}$: 5.59 Geometric Mean: $3.89 \times 10^5$ | | |

CFU = Colony Forming Units

TABLE 13

| NEUTRALIZATION CONFIRMATION CONTROL RESULTS | | | | |
|---|---|---|---|---|
| | | Neutralization Confirmation (CFU) | | Pass/ Fail |
| Test Substance | Test Organism | Numbers Control | Test Substance Results | ($Log_{10}$ Difference) |
| Zinc chloride (with BioCartilage ®) | *Staphylococcus aureus* (ATCC 6538) | 36, 29 | 38, 36 | Pass (−0.05) |
| Zinc chloride (with Amnion Matrix) | | 36, 29 | 59, 46 | Pass (−0.20) |

CFU = Colony Forming Units

Table 14 shows test results for *Staphylococcus aureus* for the BioCartilage® experiments of this example. Table 15 shows test results for *Staphylococcus aureus* for the Amnion Matrix experiments of this example. Table 16 shows calculated data of percent and Log 10 reduction for the test results shown in Table 14. Table 17 shows calculated data of percent and Log 10 reduction for the test results shown in Table 15.

TABLE 14

SHOWS TEST RESULTS FOR ZINC CHLORIDE (with BioCartilage ®)

| DILUTION (VOLUME PLATED) | Test Organism: *Staphylococcus aureus* (ATCC 6538) Number of Survivors Exposure Time | | | |
|---|---|---|---|---|
| | 6 hours | | 24 hours | |
| | Replicate 1 | Replicate 2 | Replicate 1 | Replicate 2 |
| Test Substance: 0.3% Zinc chloride with BioCartilage ® | | | | |
| $10^0$ (1.00 mL) | 35, 42 | 51, 28 | 0, 0 | 0, 0 |
| $10^0$ (0.100 mL) | 0, 0 | 0, 0 | 0, 0 | 0, 0 |
| $10^1$ (0.100 mL) | 0, 0 | 0, 0 | 0, 0 | 0, 0 |
| $10^2$ (0.100 mL) | 0, 0 | 0, 0 | 0, 0 | 0, 0 |
| $10^3$ (0.100 mL) | 0, 0 | 0, 0 | 0, 0 | 0, 0 |
| Test Substance: 0.5% Zinc chloride with BioCartilage ® | | | | |
| $10^0$ (1.00 mL) | 29, 21 | 35, 41 | 0, 0 | 0, 0 |
| $10^0$ (0.100 mL) | 0, 0 | 0, 0 | 0, 0 | 0, 0 |
| $10^1$ (0.100 mL) | 0, 0 | 0, 0 | 0, 0 | 0, 0 |
| $10^2$ (0.100 mL) | 0, 0 | 0, 0 | 0, 0 | 0, 0 |
| $10^3$ (0.100 mL) | 0, 0 | 0, 0 | 0, 0 | 0, 0 |

TABLE 15

SHOWS TEST RESULTS FOR ZINC CHLORIDE (with Amnion Matrix)

| DILUTION (VOLUME PLATED) | Test Organism: *Staphylococcus aureus* (ATCC 6538) Number of Survivors Exposure Time | | | |
|---|---|---|---|---|
| | 6 hours | | 24 hours | |
| | Replicate 1 | Replicate 2 | Replicate 1 | Replicate 2 |
| Test Substance: 0.3% Zinc chloride with Amnion Matrix | | | | |
| $10^0$ (1.00 mL) | 8, 7 | 19, 18 | 0, 0 | 0, 0 |
| $10^0$ (0.100 mL) | 0, 0 | 0, 0 | 0, 0 | 0, 0 |
| $10^1$ (0.100 mL) | 0, 0 | 0, 0 | 0, 0 | 0, 0 |
| $10^2$ (0.100 mL) | 0, 0 | 0, 0 | 0, 0 | 0, 0 |
| $10^3$ (0.100 mL) | 0, 0 | 0, 0 | 0, 0 | 0, 0 |
| Test Substance: 0.5% Zinc chloride with Amnion Matrix | | | | |
| $10^0$ (1.00 mL) | 84, 74 | 4, 2 | 0, 0 | 0, 0 |
| $10^0$ (0.100 mL) | 0, 0 | 0, 0 | 0, 0 | 0, 0 |
| $10^1$ (0.100 mL) | 0, 0 | 0, 0 | 0, 0 | 0, 0 |
| $10^2$ (0.100 mL) | 0, 0 | 0, 0 | 0, 0 | 0, 0 |
| $10^3$ (0.100 mL) | 0, 0 | 0, 0 | 0, 0 | 0, 0 |

TABLE 16

CALCULATED DATA FOR ZINC CHLORIDE (with BioCartilage ®)

| Test Substance | Exposure Time | CFU/mL in Test Population Control ($Log_{10}$) | CFU/mL of Survivors | $Log_{10}$ Survivors | Geometric Mean (Average $Log_{10}$) | Percent Reduction ($Log_{10}$ Reduction) |
|---|---|---|---|---|---|---|
| 0.3% Zinc chloride | 6 hours | $3.89 \times 10^5$ | $3.9 \times 10^2$ | 2.59 | $3.98 \times 10^2$ | >99.8% |
| with BioCartilage ® | | (5.59) | $4.0 \times 10^2$ | 2.60 | (2.60) | (2.99) |
| | 24 hours | | <5 | <0.70 | <5.01 | >99.99% |
| | | | <5 | <0.70 | (<0.70) | (>4.89) |
| 0.5% Zinc chloride | 6 hours | | $2.5 \times 10^2$ | 2.40 | $3.09 \times 10^2$ | 99.9% |
| with BioCartilage ® | | | $3.8 \times 10^2$ | 2.58 | (2.49) | (3.10) |

TABLE 16-continued

CALCULATED DATA FOR ZINC CHLORIDE (with BioCartilage®)

| Test Substance | Exposure Time | CFU/mL in Test Population Control ($Log_{10}$) | CFU/mL of Survivors | $Log_{10}$ Survivors | Geometric Mean (Average $Log_{10}$) | Percent Reduction ($Log_{10}$ Reduction) |
|---|---|---|---|---|---|---|
| | 24 hours | | <5 | <0.70 | <5.01 | >99.99% |
| | | | <5 | <0.70 | (<0.70) | (>4.89) |

CFU = Colony Forming Units
A value of <1 was used in place of zero for calculation purposes.
The geometric mean and average $log_{10}$ values were used for the population control.
The geometric mean and average $log_{10}$ values were used for the test replicates to determine reductions.

TABLE 17

CALCULATED DATA FOR ZINC CHLORIDE (with Amnion Matrix)

| Test Substance | Exposure Time | CFU/mL in Test Population Control ($Log_{10}$) | CFU/mL of Survivors | $Log_{10}$ Survivors | Geometric Mean (Average $Log_{10}$) | Percent Reduction ($Log_{10}$ Reduction) |
|---|---|---|---|---|---|---|
| 0.3% Zinc chloride | 6 hours | $3.89 \times 10^5$ | $8 \times 10^1$ | 1.90 | $1.23 \times 10^2$ | >99.9% |
| with Amnion Matrix | | (5.59) | $1.9 \times 10^2$ | 2.28 | (2.09) | (3.50) |
| | 24 hours | | <5 | <0.70 | <5.01 | >99.99% |
| | | | <5 | <0.70 | (<0.70) | (>4.89) |
| 0.5% Zinc chloride | 6 hours | | $7.9 \times 10^2$ | 2.90 | $1.55 \times 10^2$ | >99.9% |
| with Amnion Matrix | | | $3 \times 10^1$ | 1.48 | (2.19) | (3.40) |
| | 24 hours | | <5 | <0.70 | <5.01 | >99.99% |
| | | | <5 | <0.70 | (<0.70) | (>4.89) |

CFU = Colony Forming Units
A value of <1 was used in place of zero for calculation purposes.
The geometric mean and average $log_{10}$ values were used for the population control.
The geometric mean and average $log_{10}$ values were used for the test replicates to determine reductions.

It is to be understood that the above-described embodiments are illustrative of only a few of the many possible specific embodiments, which can represent applications of the principles of the invention. Numerous and varied other arrangements can be readily devised in accordance with these principles by those skilled in the art without departing from the spirit and scope of the invention.

What is claimed is:

1. A method for preparing allograft tissue, comprising:
providing allograft tissue; and
directly applying to the allograft tissue an antimicrobial solution comprising from about 0.1% to about 0.5% zinc compound by soaking or washing the allograft tissue in the antimicrobial solution for about 2 hours to about 24 hours, thereby causing the zinc compound to directly associate with the allograft tissue and modify the surface of the allograft tissue,
wherein the antimicrobial solution exhibits antimicrobial activity of inhibiting or controlling growth of microbial organisms in the allograft tissue and provides deep tissue cleaning.

2. The method of claim 1 wherein the zinc compound is selected from the group consisting of zinc chloride, zinc sulfate, zinc phosphate, zinc carbonate, and zinc nitrate, zinc chlorate, zinc chromate and combinations thereof.

3. The method of claim 2 wherein the zinc compound is zinc chloride.

4. The method of claim 1 wherein the zinc compound is a zinc salt selected from the group consisting of zinc acetate, zinc formate, zinc propionate, zinc gluconate, bis(maltolato) zinc, zinc acexamate, zinc aspartate, bis(maltolato)zinc(II) [Zn(ma)2], bis(2-hydroxypyridine-N-oxido)zinc(II) [Zn(hpo)2], bis(allixinato)Zn(II) [Zn(alx)2], bis(6-methylpicolinato)Zn(II) [Zn(6mpa)2], bis(aspirinato)zinc(II), bis (pyrrole-2-carboxylato) zinc [Zn(pc)2], bis(alpha-furonic acidato)zinc [Zn(fa)2], bis(thiophene-2-carboxylato) zinc [Zn(tc)2], bis(thiophene-2-acetato)zinc [Zn(ta)2], (N-acetyl-L-cysteinato) Zn(II) [Zn(nac)], zinc(II)/poly(γ-glutamic acid) [Zn(γ-pga)], bis(pyrrolidine-N-dithiocarbamate) zinc (II) [Zn(pdc)2], zinc(II) L-lactate [Zn(lac)2], zinc(II) D-(2)-quinic acid [Zn(qui)2], bi s(1,6-dimethyl-3-hydroxy-5-methoxy-2-pentyl-1,4-dihydropyridine-4-thion-ato) zinc(II) [Zn(tanm)2], β-alanyl-L-histidinato zinc(II) (AHZ) and combinations thereof.

5. The method of claim 1 wherein the allograft tissue is selected from the group consisting of allograft bone, allograft cartilage, amniotic tissue, ligament tissue, tendon tissue, porous tissue and soft tissue.

6. The method of claim 1 wherein the allograft tissue is allograft bone.

7. The method of claim 1 wherein the allograft tissue is amniotic tissue.

8. The method of claim 1 wherein the allograft tissue is allograft cartilage.

9. The method of claim 1 wherein the microbial organisms are selected from the group consisting of *Pseudomonas aeruginosa, Staphylococcus aureus, Aspergillus brasiliensis* spores and *Escherichia coli.*

10. The method of claim 1 wherein the step of applying comprises directly applying to the allograft tissue the antimicrobial solution comprising from about 0.1% to about 0.5% zinc chloride by soaking the allograft tissue in the antimicrobial solution for about 2 hours to about 24 hours.

11. The method of claim 1 wherein the step of applying comprises directly applying to the allograft tissue the antimicrobial solution comprising from about 0.3% to about 0.5% zinc chloride by soaking the allograft tissue in the antimicrobial solution for about 2 hours to about 6 hours.

12. The method of claim 1 wherein the antimicrobial solution comprises $Zn^{2+}$ ions.

13. The method of claim 1 wherein the antimicrobial solution further comprises a pharmaceutically acceptable vehicle, excipient, diluent or adjuvant.

* * * * *

UNITED STATES PATENT AND TRADEMARK OFFICE
CERTIFICATE OF CORRECTION

PATENT NO. : 11,224,678 B2
APPLICATION NO. : 15/425617
DATED : January 18, 2022
INVENTOR(S) : Joseph Benevenia et al.

It is certified that error appears in the above-identified patent and that said Letters Patent is hereby corrected as shown below:

In the Claims

At Column 11, Line number 64, after 4., replace Claim 4 with the following:
--- The method of claim 1 wherein the zinc compound is a zinc salt selected from the group consisting of zinc acetate, zinc formate, zinc propionate, zinc gluconate, bis(maltolato)zinc, zinc acexamate, zinc aspartate, bis(maltolato)zinc(II) [Zn(ma)2], bis(2-hydroxypyridine-N-oxido)zinc(II) [Zn(hpo)2], bis(allixinato)Zn(II) [Zn(alx)2], bis(6-methylpicolinato)Zn(II) [Zn(6mpa)2], bis(aspirinato)zinc(II), bis(pyrrole-2-carboxylato) zinc [Zn(pc)2], bis(alpha-furonic acidato)zinc [Zn(fa)2], bis(thiophene-2-carboxylato) zinc [Zn(tc)2], bis(thiophene-2-acetato)zinc [Zn(ta)2], (N-acetyl-L-cysteinato) Zn(II) [Zn(nac)], zinc(II)/poly(γ-glutamic acid) [Zn(γ-pga)], bis(pyrrolidine-N-dithiocarbamate) zinc(II) [Zn(pdc)2], zinc(II) L-lactate [Zn(lac)2], zinc(II) D-(2)-quinic acid [Zn(qui)2], bis(1,6-dimethyl-3-hydroxy-5-methoxy-2-pentyl-1,4-dihydropyridine-4-thion-ato) zinc(II) [Zn(tanm)2], β-alanyl-L-histidinato zinc(II) (AHZ) and combinations thereof. ---

Signed and Sealed this
Fourteenth Day of June, 2022

Katherine Kelly Vidal

Katherine Kelly Vidal
*Director of the United States Patent and Trademark Office*